US010028522B2

(12) United States Patent
Coleman, III et al.

(10) Patent No.: US 10,028,522 B2
(45) Date of Patent: Jul. 24, 2018

(54) TOBACCO SEED-DERIVED COMPONENTS AND MATERIALS

(71) Applicant: R. J. REYNOLDS TOBACCO COMPANY, Winston-Salem, NC (US)

(72) Inventors: William Monroe Coleman, III, Winston-Salem, NC (US); Michael Francis Dube, Winston-Salem, NC (US); Darlene Madeline Lawson, Kernersville, NC (US)

(73) Assignee: R. J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 15/209,981

(22) Filed: Jul. 14, 2016

(65) Prior Publication Data

US 2016/0316814 A1  Nov. 3, 2016

Related U.S. Application Data

(62) Division of application No. 12/764,613, filed on Apr. 21, 2010, now Pat. No. 9,402,415.

(51) Int. Cl.
| | | |
|---|---|---|
| A24B 15/24 | (2006.01) | |
| A24B 15/30 | (2006.01) | |
| C12P 7/22 | (2006.01) | |
| C12P 7/64 | (2006.01) | |
| C12P 13/04 | (2006.01) | |

(52) U.S. Cl.
CPC ............ *A24B 15/307* (2013.01); *A24B 15/24* (2013.01); *A24B 15/302* (2013.01); *C12P 7/22* (2013.01); *C12P 7/6409* (2013.01); *C12P 7/6427* (2013.01); *C12P 7/6445* (2013.01); *C12P 13/04* (2013.01)

(58) Field of Classification Search
None
See application file for complete search history.

(56) References Cited

U.S. PATENT DOCUMENTS

| | | | |
|---|---|---|---|
| 3,424,171 A | 1/1969 | Rooker | |
| 4,008,210 A | 2/1977 | Steele et al. | |
| 4,009,290 A | 2/1977 | Okumori et al. | |
| 4,045,879 A | 9/1977 | Witte | |
| 4,083,372 A | 4/1978 | Boden | |
| 4,122,104 A | 10/1978 | Witte | |
| 4,144,895 A | 3/1979 | Fiore | |
| 4,150,677 A | 4/1979 | Osborne, Jr. et al. | |
| 4,267,847 A | 5/1981 | Reid | |
| 4,289,147 A | 9/1981 | Wildman et al. | |
| 4,298,540 A | 11/1981 | Youn et al. | |
| 4,351,346 A | 9/1982 | Brummer et al. | |
| 4,359,059 A | 11/1982 | Brummer et al. | |
| 4,359,417 A | 11/1982 | Karnofsky et al. | |
| 4,456,556 A | 6/1984 | Grimsby | |
| 4,456,557 A | 6/1984 | Grimsby | |
| 4,466,923 A | 8/1984 | Friedrich | |
| 4,506,682 A | 3/1985 | Muller | |
| 4,515,726 A | 5/1985 | Sullivan | |
| 4,589,428 A | 5/1986 | Keritsis | |
| 4,605,016 A | 8/1986 | Soga et al. | |
| 4,716,911 A | 1/1988 | Poulose et al. | |
| 4,727,889 A | 3/1988 | Niven, Jr. et al. | |
| 4,836,224 A | 6/1989 | Lawson et al. | |
| 4,847,106 A | 7/1989 | Pike et al. | |
| 4,887,618 A | 12/1989 | Bernasek et al. | |
| 4,941,484 A | 7/1990 | Clapp et al. | |
| 4,967,771 A | 11/1990 | Fagg et al. | |
| 5,018,540 A | 5/1991 | Grubbs et al. | |
| 5,027,837 A | 7/1991 | Clearman et al. | |
| 5,074,319 A | 12/1991 | White et al. | |
| 5,077,071 A | 12/1991 | Strop | |
| 5,099,862 A | 3/1992 | White et al. | |
| 5,235,992 A | 8/1993 | Sensabaugh, Jr. | |
| 5,296,621 A | 3/1994 | Roos et al. | |
| 5,301,694 A | 4/1994 | Raymond et al. | |

(Continued)

FOREIGN PATENT DOCUMENTS

| | | | |
|---|---|---|---|
| JP | 59-28465 A | 2/1984 | |
| WO | WO 2005/041699 A2 | 5/2005 | |

(Continued)

OTHER PUBLICATIONS

Coleman, III et al., "Headspace Solid-Phase Microextraction Analysis of Artificial Flavors", *J. Sci Food Agric*, 2005, vol. 85, pp. 2645-2654.

Coleman, III et al., "The Use of a Non-equilibrated Solid Phase Microextraction Method to Quantitatively Determine the Off-notes in Mint and other Essential Oils", *J. Sci Food Agric*, 2004, vol. 84, pp. 1223-1228.

Frega et al., "Chemical Composition of Tobacco Seeds (*Nicotiana tobacum* L. )", *JAOCS.*, 1991, vol. 68, No. 1, pp. 29-33.

Giannelos et al., "Tobacco Seed Oil as an Alternative Diesel Fuel: Physical and Chemical Properties", *Industrial Crops and Products*, 2002, vol. 16, pp. 1-9.

(Continued)

*Primary Examiner* — Cynthia Szewczyk
(74) *Attorney, Agent, or Firm* — Womble Bond Dickinson (US) LLP

(57) ABSTRACT

A tobacco composition for use in a smoking article or a smokeless tobacco composition is provided, the composition including a component derived from a seed of the *Nicotiana* species. The component can be a seed of the *Nicotiana* species or a portion thereof in particulate form or in the form of seed isolate derived from a seed of the *Nicotiana* species. In certain embodiments, the seed isolate is in the form of a chemically transformed seed isolate, the chemical transformation being selected from hydrogenation, acid/base reaction, hydrolysis, thermal treatment, and enzymatic treatment. The invention also provides smoking articles and smokeless tobacco compositions that include the seed components described herein, and methods for preparing a component derived from a seed of the *Nicotiana* species for addition to a tobacco composition.

11 Claims, No Drawings

(56) References Cited

U.S. PATENT DOCUMENTS

| | | | |
|---|---|---|---|
| 5,318,050 | A | 6/1994 | Gonzalez-Parra et al. |
| 5,343,879 | A | 9/1994 | Teague |
| 5,360,022 | A | 11/1994 | Newton et al. |
| 5,387,416 | A | 2/1995 | White et al. |
| 5,397,571 | A | 3/1995 | Roland et al. |
| 5,435,325 | A | 7/1995 | Clapp et al. |
| 5,445,169 | A | 8/1995 | Brinkley et al. |
| 5,547,997 | A | 8/1996 | Kludas |
| 5,724,998 | A | 3/1998 | Gellatly et al. |
| 5,932,095 | A | 8/1999 | Walters et al. |
| 6,083,729 | A | 7/2000 | Martin et al. |
| 6,131,584 | A | 10/2000 | Lauterbach |
| 6,225,483 | B1 | 5/2001 | Franke |
| 6,298,858 | B1 | 10/2001 | Coleman, III et al. |
| 6,298,859 | B1 | 10/2001 | Kierulff et al. |
| 6,403,126 | B1 | 6/2002 | Webster et al. |
| 6,414,172 | B1 | 7/2002 | Garcés et al. |
| 6,417,157 | B1 | 7/2002 | Wadsworth et al. |
| 6,495,175 | B2 | 12/2002 | Rao et al. |
| 6,499,489 | B1 | 12/2002 | Coleman, III |
| 6,504,085 | B1 | 1/2003 | Howard |
| 6,591,841 | B1 | 7/2003 | White et al. |
| 6,772,767 | B2 | 8/2004 | Mua et al. |
| 6,800,318 | B2 | 10/2004 | Kapila et al. |
| 6,860,998 | B1 | 3/2005 | Wilde |
| 6,861,077 | B1 | 3/2005 | Cannell et al. |
| 6,953,040 | B2 | 10/2005 | Atchley et al. |
| 7,032,601 | B2 | 4/2006 | Atchley et al. |
| 7,074,449 | B1 | 7/2006 | Holley et al. |
| 7,105,173 | B1 | 9/2006 | Rolling |
| 7,156,981 | B2 | 1/2007 | Wilde et al. |
| 7,198,808 | B2 | 4/2007 | Krasutsky et al. |
| 7,337,782 | B2 | 3/2008 | Thompson |
| 7,615,657 | B2 | 11/2009 | Bathurst et al. |
| 7,741,500 | B2 | 6/2010 | Arhancet et al. |
| 7,798,153 | B2 | 9/2010 | Lawrence, Jr. |
| 7,810,507 | B2 | 10/2010 | Dube et al. |
| 7,819,124 | B2 | 10/2010 | Strickland et al. |
| 2002/0121628 | A1 | 9/2002 | Kapila et al. |
| 2004/0009242 | A1 | 1/2004 | Krasutsky et al. |
| 2004/0020503 | A1 | 2/2004 | Williams |
| 2004/0173228 | A1 | 9/2004 | Coleman, III |
| 2005/0042347 | A1 | 2/2005 | Bathurst et al. |
| 2005/0147722 | A1 | 7/2005 | Fan et al. |
| 2006/0191548 | A1 | 8/2006 | Strickland et al. |
| 2006/0198873 | A1 | 9/2006 | Chan et al. |
| 2007/0062549 | A1 | 3/2007 | Holton, Jr. et al. |
| 2007/0184123 | A1 | 8/2007 | Soulimani |
| 2007/0186941 | A1 | 8/2007 | Holton, Jr. et al. |
| 2008/0029116 | A1 | 2/2008 | Robinson et al. |
| 2008/0196730 | A1 | 8/2008 | Engstrom et al. |
| 2010/0037903 | A1 | 2/2010 | Coleman, III et al. |
| 2010/0040758 | A1 | 2/2010 | Savngikar et al. |
| 2010/0058655 | A1 | 3/2010 | Fogher |
| 2010/0119613 | A1 | 5/2010 | Gruber et al. |
| 2010/0203004 | A1 | 8/2010 | Simonnet et al. |
| 2010/0239726 | A1 | 9/2010 | Pertsovich |
| 2011/0259353 | A1 | 10/2011 | Coleman, III et al. |

FOREIGN PATENT DOCUMENTS

| | | |
|---|---|---|
| WO | WO 2007/012980 A1 | 2/2007 |
| WO | WO 2009/110775 A1 | 9/2009 |
| WO | WO 2010/093229 A1 | 8/2010 |

OTHER PUBLICATIONS

Ishikawa et al., "Water-Soluble Constituents of Dill", *Chem. Pharm. Bull.*, 2002, vol. 50 No. 4, pp. 501-507.

Majdi et al., Supercritical Fluid Extraction of Tobacco See Oil and Its Composition with Solvent Extraction Methods, *J. Agr. Sci. Tech.*, 2012, pp. 1043-1051, Vo. 14.

Mukhtar et al., "Fatty Acid Composition of Tobacco Seed Oil and Synthesis of Alkyd Resin", *Chin. J. of Chem.*, 2007, vol. 25, No. 5, pp. 705-708.

Ochiai, Nobuo, Ph,D., "Take Two" *Gerstel Solutions Worldwide*, 2006, No. 6, pp. 17-19.

Patel et al., "Production Potential and Quality Aspects of Tobacco Seed Oil", *Tob. Res.*, 1998, vol. 24, No. 1, pp. 44-49.

Sahraoui et al., "Improved Microwave Steam Distillation Apparatus for Isolation of Essential Oils Comparison with Conventional Steam Distillation", *J. Chromatogr A.*, 2008, vol. 1210, pp. 229-233.

Stanisavljevic et al., "Comparison of Techniques for the Extraction of Tobacco Seed Oil," *Eur. J. Lipid Sci. Technol.*, 2009, 111, pp. 513-518.

Stanisavljevic et al., "Comparison of techniques for the Extraction of Tobacco Seed Oil", *Eur. J. Lipid Sci. Technol.*, 2009, vol. 111, pp. 1-6.

Stanisavljević et al., Ultrasonic extraction of oil from tobacco (*Nicotiana tabacum* L.) seeds, *Ultrasonics Sonochemistry*, 2007, pp. 646-652, vol. 14, No. 5.

Tienpont et al., "Stir Bar Sorptive Extraction-Thermal Desorption-Capillary GC-MS Applied to Biological Fluids", *Anal. Bioanal. Chem.*, 2002, vol. 373, pp. 46-55.

TOBACCO SEED-DERIVED COMPONENTS AND MATERIALS

CROSS-REFERENCE TO RELATED APPLICATIONS

This application is a divisional application of U.S. application Ser. No. 12/764,613, filed Apr. 21, 2010, which is incorporated by reference herein in its entirety.

FIELD OF THE INVENTION

The present invention relates to products made or derived from tobacco, or that otherwise incorporate tobacco, and are intended for human consumption. Of particular interest are ingredients or components obtained or derived from plants or portions of plants from the *Nicotiana* species.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco, and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, $3^{rd}$ Ed., p. 43 (1990) and *Tobacco Production, Chemistry and Technology*, Davis et al. (Eds.) p. 346 (1999).

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. See also, Leffingwell et al., *Tobacco Flavoring for Smoking Products*, R. J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Pat. Appl. Publication No. 2004/0173228 to Coleman, III; and U.S. application Ser. No. 12/191,751 to Coleman, III et al., filed Aug. 14, 2008, each of which is incorporated herein by reference. Additionally, examples of representative components that can be employed as so-called natural tar diluents in tobacco products are set in PCT WO 2007/012980 to Lipowicz, which is incorporated herein by reference.

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. Appl. Pub. Nos. 2005/0244521 to Strickland et al.; 2008/0196730 to Engstrom et al.; and 2009/0293889 to Kumar et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See, for example, the types of smokeless tobacco formulations, ingredients, and processing methodologies set forth in U.S. Pat. No. 6,953,040 to Atchley et al. and U.S. Pat. No. 7,032,601 to Atchley et al., each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R. J. Reynolds Tobacco Company.

The sensory attributes of smokeless tobacco can also be enhanced by incorporation of certain flavoring materials. See, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

It would be desirable to provide methods for altering the character and nature of tobacco (and tobacco compositions and formulations) useful in the manufacture of smoking articles and/or smokeless tobacco products.

SUMMARY OF THE INVENTION

The present invention provides materials from *Nicotiana* species (e.g., tobacco-derived materials) comprising isolated components from plants of the *Nicotiana* species useful for incorporation into tobacco compositions utilized in a variety of tobacco products, such as smoking articles and smokeless tobacco products. The invention also provides methods for isolating components from *Nicotiana* species (e.g., tobacco materials), and methods for processing those components and tobacco materials incorporating those components. For example, tobacco-derived materials can be prepared by subjecting at least a portion of a tobacco plant (e.g., leaves, stalks, roots, or stems), but most preferably at least a portion of the tobacco seed, to a separation process, which typically can include multiple sequential extraction steps, in order to isolate desired components of the tobacco material.

The use of *Nicotiana*-derived (e.g., tobacco-derived) materials of the present invention enables the preparation of tobacco compositions for smoking articles or smokeless tobacco compositions that are derived substantially or even entirely from *Nicotiana* materials. For example, a tobacco composition can incorporate tobacco or tobacco-derived material of some form, including isolated components from *Nicotiana* species, such that at least about 80 weight percent, more typically at least about 90 weight percent, or even at least about 95 weight percent (on a dry weight basis), of that tobacco composition consists of tobacco-derived material.

In one aspect, the invention provides a tobacco composition for use in a smoking article or a smokeless tobacco composition comprising a tobacco material and a seed component derived from a seed of the *Nicotiana* species, wherein the seed component is (i) a seed of the *Nicotiana* species or a portion thereof in particulate form; or (ii) a seed isolate derived from a seed of the *Nicotiana* species.

In certain embodiments, the seed isolate is formed using techniques adapted for expressing lipids from the seed, such as high pressure squeezing or cold pressing. Alternatively, the seed isolate is formed by extracting components from the seed using appropriate extraction techniques and solvents. Exemplary solvents include hydrocarbons such as heptane and hexane. Other separation processes could be used, such as chromatography, distillation, filtration, recrystallization, solvent-solvent partitioning, and combinations thereof. The seed isolate formed using an extraction process can be either the solvent-soluble portion or the insoluble residue of seed material remaining after solvent extraction. The seed isolate formed using a pressing process can be either the lipid-containing portion of the seed expressed from the pressed seed material or can be the seed residue remaining after pressing.

The seed isolate prepared according to the invention typically contains at least one compound useful for enhancing the chemical and/or physical characteristics of the tobacco composition to which the seed isolate is added. Exemplary compounds that are components of seeds of the *Nicotiana* species, and that can be separated and isolated, include fatty acids (e.g., linoleic acid, oleic acid, palmitic acid and stearic acid), triglycerides, polyphenols, and amino acids.

Seed isolates can be used as such, or in the form of a chemically transformed seed isolate. The chemical transformation typically results in a change in the chemical composition of the seed isolate, such as an increase in the amount of certain compounds that have desirable sensory characteristics (e.g., aromatic or flavorful compounds). For example, representative chemical transformations of seed isolates include hydrogenation, acid/base reaction, hydrolysis, thermal treatment, enzymatic treatment, and combinations of such steps. The chemically transformed seed isolate can be a seed isolate subjected to a process selected from the group consisting of esterification, transesterification, isomeric conversion, acetal formation, acetal decomposition, and combinations thereof.

In one embodiment, the seed component can comprise a seed isolate comprising lipids expressed from a seed. Optionally, various isolated lipid components of the seed can be subjected to hydrogenation in order to alter the degree of saturation of those components, and hence alter the physical form or behavior of those components. In other words, the chemically transformed seed isolate may comprise a hydrogenated lipid composition isolated from a seed of the *Nicotiana* species.

In further embodiments, the seed isolate can be derived from an enzymatically-treated seed or an enzymatically-treated seed isolate. In another embodiment, the seed component is a seed isolate in the form of an extract from a seed material, such as extracts formed by solvent extraction using polar solvents, non-polar organic solvents, or supercritical fluids, and the extract can thereafter be subjected to an enzymatic treatment.

The chemical transformation process can occur prior to, simultaneously with, or after a separation step to form a seed isolate. In other words, a seed material that has not been subjected to a separation step (e.g., a seed material in particulate form) can be subjected to a chemical transformation step, such as an enzymatic treatment, prior to subjecting the seed material to a separation process, such as extraction or pressing, to form a seed isolate. Alternatively, the seed material could be subjected to a separation process to produce a seed isolate and thereafter the seed isolate could be subjected to a chemical transformation treatment. Still further, multiple separation processes and multiple chemical transformation processes could be used in various sequences.

The invention also provides smoking articles and smokeless tobacco compositions that include the seed components or seed isolates of the types described herein. For example, a tobacco composition can incorporate a seed isolate within a casing formulation or a top dressing formulation applied to tobacco strip or as a component of a reconstituted tobacco material. Smoking articles or smokeless tobacco compositions incorporating a seed component typically comprise between about 5 ppm and about 5 weight percent of the seed component, based on the total dry weight of the total amount of tobacco material of the smoking article or smokeless tobacco product. Alternatively, where the tobacco composition includes one or more capsules containing an internal payload (e.g., a flavorant-containing payload), the seed component can be a seed isolate contained within the internal payload.

The present invention, in another aspect, relates to various methods for preparing isolates obtained or derived from seed of the *Nicotiana* species. In one embodiment, the method comprises (1) isolating components of a harvested seed of the *Nicotiana* species by subjecting the harvested seed or a portion thereof to cold pressing, solvent extraction, chromatography, distillation, filtration, recrystallization, solvent-solvent partitioning, or a combination thereof to form a seed isolate; and (2) chemically transforming the harvested seed prior to said isolating step or chemically transforming the seed isolate after said isolating step, wherein the chemically transforming step is a treatment selected from the group consisting of hydrogenation, acid/base reaction, hydrolysis, thermal treatment, enzymatic treatment, or a combination thereof. The method can further include the step of adding a chemically transformed seed isolate to a tobacco composition adapted for use in a smoking article or a smokeless tobacco composition.

In one embodiment, the isolating step comprises solvent extraction of a harvested seed or a portion thereof using a polar solvent or a non-polar organic solvent. In another embodiment, the chemically transforming step comprises subjecting the harvested seed or a portion thereof to enzymatic treatment to form an enzymatically-treated seed material, and the isolating step comprises subjecting the enzymatically-treated seed material to solvent extraction to form a chemically transformed seed isolate. In yet another embodiment, the chemically transforming step comprises freezing a harvested seed or a portion thereof to form a frozen seed material, processing the frozen seed into a particulate form, and subjecting the particulate seed material to an enzymatic treatment to chemically alter the particulate seed material; and the isolating step comprises extracting the particulate seed material with a solvent to produce a chemically transformed seed isolate. Still further, one embodiment includes a chemically transforming step that comprises enzymatic treatment of the harvested seed or a portion thereof with a hydrolyase, a glycosidase, or a glucocidase. In a further embodiment, the isolating step comprises cold pressing the harvested seed or a portion thereof in order to express lipids from the harvested seed to form a lipid-containing seed isolate. Optionally, the lipid-containing seed isolate is subjected to hydrogenation in order to alter the degree of saturation of the lipids within the lipid-containing seed isolate.

In another embodiment, the method comprises:

i) receiving a harvested seed of the *Nicotiana* species or a portion thereof;

ii) processing the harvested seed or portion thereof by at least one of subdividing the harvested seed or portion thereof to form a particulate seed material or separating a seed isolate from the harvested seed by subjecting the harvested seed or a portion thereof to cold pressing, solvent extraction, chromatography, distillation, filtration, recrystallization, solvent-solvent partitioning, or a combination thereof; and iii) adding the particulate seed material or seed isolate produced in step ii) to a tobacco composition adapted for use in a smoking article or a smokeless tobacco composition.

Additionally, in certain embodiments, the seed isolate produced in step ii) above can be subjected to chemical transformation processing steps prior to step iii). In one particular embodiment, the separating step comprises subjecting a harvested seed or a portion thereof to enzymatic treatment to form an enzymatically-treated seed material and subjecting the enzymatically-treated seed material to solvent extraction to form the seed isolate.

DETAILED DESCRIPTION OF THE PREFERRED EMBODIMENTS

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative types of plants from the *Nicotiana* species are set forth in Goodspeed, *The Genus Nicotiana*, (*Chonica Botanica*) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Of particular interest are *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata*, and *N. x sanderae*. Also of interest are *N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. rustica, N. simulans, N. stocktonii, N. suaveolens, N. tabacum, N. umbratica, N. velutina*, and *N. wigandioides*. Other plants from the *Nicotiana* species include *N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia* and *N. spegazzinii*.

*Nicotiana* species can be derived using genetic-modification or crossbreeding techniques (e.g., tobacco plants can be genetically engineered or crossbred to increase or decrease production of certain components or to otherwise change certain characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al.; and U.S. Pat. No. 7,230,160 to Benning et al.; US Patent Appl. Pub. No. 2006/0236434 to Conkling et al.; and PCT WO 2008/103935 to Nielsen et al.

For the preparation of smokeless and smokable tobacco products, it is typical for harvested plants of the *Nicotiana* species to be subjected to a curing process. Descriptions of various types of curing processes for various types of tobaccos are set forth in *Tobacco Production, Chemistry and Technology*, Davis et al. (Eds.) (1999). Exemplary techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. See, also, for example, U.S. Pat. No. 7,650,892 to Groves et al., which is incorporated herein by reference. Representative techniques and conditions for air curing tobacco are set forth in Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing. Preferably, harvested tobaccos that are cured are then aged.

At least a portion of the plant of the *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing seeding, is commencing flowering, or the like.

At least a portion of the plant of the *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position.

After harvest, the plant of the *Nicotiana* species, or portion thereof, can be used in a green form (e.g., tobacco can be used without being subjected to any curing process). For example, tobacco in green form can be frozen, freeze-dried, subjected to irradiation, yellowed, dried, cooked (e.g., roasted, fried or boiled), or otherwise subjected to storage or treatment for later use. Such tobacco also can be subjected to aging conditions.

In accordance with the present invention, a tobacco product incorporates tobacco that is combined with some form of the seed obtained from, or derived from, a plant of at least one *Nicotiana* species. That is, a portion of the tobacco product can be composed of some form of the seed of a *Nicotiana* species, such as parts or pieces of the seed, or processed materials incorporating processed seed or components thereof. At least a portion of the tobacco product can be composed of components of the seed, such as ingredients removed from the seed (e.g., by extraction, distillation, or other types of processing techniques). At least a portion of the tobacco product can be composed of components derived from the seed, such as components collected after subjecting the seed to chemical reaction or after subjecting components collected from the seed to chemical reaction (e.g., acid/base reaction conditions or enzymatic treatment).

The seed material used in the invention is provided from the seed of the plant of the *Nicotiana* species, which is the characteristic reproductive structure of the plant (e.g., seed producing structure). See, for example, Frega et al., *JAOCS*, 68, 29-33 (1991); Patel et al., *Tob. Res.*, 24, 44-49 (1998); Giannelos et al., *Ind. Crops Prod.*, 16, 1-9 (2002); Mukhtar et al., *Chinese J. Chem.*, 25, 705-708 (2007); Stanisavljevic et al., *Eur. J. Lipid Sci. Technol.*, 111, 513-518 (2009); which are incorporated herein by reference.

The *Nicotiana* species can be selected for the type of seed that it produces. For example, plants can be selected on the basis that those plants produce relatively numerous seeds, produce seed that incorporate relatively high levels of specific desired components, and the like.

The *Nicotiana* species of plant can be grown under agronomic conditions so as to promote seed and seed development. Tobacco plants can be grown in greenhouses, growth chambers, or outdoors in fields, or grown hydroponically.

The seed is harvested from the *Nicotiana* species of plant. The manner by which the seed is harvested can vary. As such, the seed is removed from the rest of the plant by cutting or breaking the so-called seed head or seed capsule from the rest of the plant. Typically, virtually all of the seed (e.g., the whole seed) can be harvested, and employed as such. The various seeds can be isolated using typical mechanical separation and collection techniques.

The time of harvest during the life cycle of the plant can vary. For example, seed can be harvested when immature, and as such, the inflorescence or flower head can be removed from the plant. Alternatively, the seed head or seed capsule can be harvested from the plant after the point that the seed has reached maturity.

The post-harvest processing of the seed can vary. After harvest, the seed, or portion thereof, can be used in the harvested form (e.g., the seed can be used without being subjected to any curing and/or aging process steps). For example, the seed can be used without being subjected to significant storage, handling or processing conditions. In certain situations, it is preferable that the fresh seed be used virtually immediately after harvest. Alternatively, for example, seed can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use.

The harvested seed can be physically processed. The seed, or parts thereof, can be further subdivided into parts or pieces (e.g., the seed can be comminuted, pulverized, milled or ground into pieces or parts that can be characterized as granules, particulates or fine powders). The seed, or parts thereof, can be subjected to external forces or pressure (e.g., by being pressed or subjected to roll treatment). When carrying out such processing conditions, the seed can have a moisture content that approximates its natural moisture content (e.g., its moisture content immediately upon harvest), a moisture content achieved by adding moisture to the seed or a moisture content that results from the drying of the seed. For example, powdered, pulverized, ground or milled pieces of seed can have moisture contents of less than about 25 weight percent, often less than about 20 weight percent, and frequently less than about 15 weight percent. Parts or pieces of the seed can be used as components of tobacco products without further processing, or alternatively the particulate seed material can be processed further prior to incorporation into a tobacco product.

The harvested seed, or components thereof, can be subjected to other types of processing conditions. For example, components of the seed can be separated from one another, or otherwise fractionated into chemical classes or mixtures of individual compounds. As used herein, an "isolated seed component" or "seed isolate" is a compound or complex mixture of compounds separated from a seed of a plant of the *Nicotiana* species. The isolated seed component can be a single compound, a homologous mixture of similar compounds (e.g., isomers of a flavorful or aromatic compound), or a heterologous mixture of dissimilar compounds (e.g., a complex mixture of various compounds of different types, preferably having desirable sensory attributes).

Examples of the types of components that can be present in a seed isolate include various fatty acids and various triglycerides. Exemplary fatty acids include palmitic acid, linoleic acid, oleic acid, caprylic acid, myristic acid, pentadecanoic acid, palmetoleic acid, heptadecanoic acid, heptadecenoic acid, elaidic acid, gamma-lenolenic acid, arachidic acid, arachidonic acid, 11-eicosenoic acid, 8,11,14-eicosatrieonic acid, 11,14,17-eicosatrienoic acid, 5,8,11,14, 17-eicosopentanoic acid, heniecosenoic acid, lignoceric acid, 4,7,10,15,19-decosahexanoic acid, and stearic acid. Exemplary triglycerides include trilinolein, palmito-di-linolein, di-palmito-linolein, tripalmitin, tristearin, and triolein. Exemplary components of seed isolates also include a variety of other compounds having flavor and aroma characteristics such as amino acids and various polyphenols.

Typical separation processes can include one or more process steps such as solvent extraction (e.g., using polar solvents, non-polar organic solvents, or supercritical fluids), chromatography, distillation, filtration, cold pressing or other pressure-based techniques, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., *LC-GC Europe*, p. 2-5 (March, 2002) and Wellings, *A Practical Handbook of Preparative HPLC* (2006), which are incorporated herein by reference. In addition, the seed or components thereof can be subjected to the types of treatments set forth in Ishikawa et al., *Chem. Pharm. Bull.*, 50, 501-507 (2002); Tienpont et al., *Anal. Bioanal. Chem.*, 373, 46-55 (2002); Ochiai, *Gerstel Solutions Worldwide*, 6, 17-19 (2006); Coleman, III, et al., *J. Sci. Food and Agric.*, 84, 1223-1228 (2004); Coleman, III et al., *J. Sci. Food and Agric.*, 85, 2645-2654 (2005); Pawliszyn, ed., *Applications of Solid Phase Microextraction, RSC Chromatography Monographs*, (Royal Society of Chemistry, UK) (1999); Sahraoui et al., *J. Chrom.*, 1210, 229-233 (2008); and U.S. Pat. No. 5,301,694 to Raymond et al., which are incorporated herein by reference. See also, for example, the types of processing techniques set forth in Frega et al., *JAOCS*, 68, 29-33 (1991); Patel et al., *Tob. Res.*, 24, 44-49 (1998); Giannelos et al., *Ind. Crops Prod.*, 16, 1-9 (2002); Mukhtar et al., *Chinese J. Chem.*, 25, 705-708 (2007); Stanisavljevic et al., *Eur. J. Lipid Sci. Technol.*, 111, 513-518 (2009); which are incorporated herein by reference.

Other methods of forming a seed isolate from a tobacco seed can be employed. For example, the method can produce a lipid-containing seed isolate (i.e., a tobacco seed-derived oil component) from a tobacco seed source. Methods of extracting oil components from plant seeds are described, for example, in U.S. Pat. No. 4,008,210 to Steele et al.; U.S. Pat. No. 4,009,290 to Okumori et al.; U.S. Pat. No. 4,045,879 to Witte; U.S. Pat. No. 4,122,104 to Witte; U.S. Pat. No. 4,298,540 to Youn et al.; U.S. Pat. No. 4,359,417 to Karnofsky et al.; U.S. Pat. No. 4,456,556 to Grimsby; U.S. Pat. No. 4,456,557 to Grimsby; U.S. Pat. No. 4,466,923 to Friedrich; U.S. Pat. No. 4,515,726 to Sullivan; U.S. Pat. No. 4,847,106 to Pike et al.; U.S. Pat. No. 5,077,071 to Strop; U.S. Pat. No. 5,296,621 to Roos et al.; U.S. Pat. No. 5,397,571 to Roland et al.; U.S. Pat. No. 5,932,095 to Walters et al.; U.S. Pat. No. 6,083,729 to Martin et al.; U.S. Pat. No. 6,225,483 to Franke; U.S. Pat. No. 6,403,126 to Webster et al.; U.S. Pat. No. 6,414,172 to Garces et al.; U.S. Pat. No. 6,417,157 to Wadsworth et al.; U.S. Pat. No. 6,495,175 to Rao et al.; U.S. Pat. No. 6,504,085 to Howard; U.S. Pat. No. 6,860,998 to Wilde; U.S. Pat. No. 7,074,449 to Holley et al.; and U.S. Pat. No. 7,156,981 to Wilde et al.; and US Patent Appl. Pub. Nos. 2002/0121628 to Kapila et al.; 2004/0009242 to Krasutsky et al.; 2005/0042347 to Bathurst et al.; 2005/0147722 to Fan et al.; and 2006/0111578 to Arhancet et al., all of which are incorporated by reference herein.

Components of the seed can be subjected to conditions so as to cause those components (whether as part of the seed or in the form of an isolated component) to undergo chemical transformation. For example, seed isolates that have been separated from the seed can be treated to cause chemical transformation or can be admixed with other ingredients. The chemical transformations or modification of the seed isolate can result in changes of certain chemical and physical properties of those seed isolates (e.g., the sensory attributes of those isolates). Exemplary chemical modification processes can be carried out by acid/base reaction, hydrolysis, heating (e.g., a thermal treatment where the seed isolate is subjected to an elevated temperature such as a temperature of at least about 50° C. or at least about 75° C. or at least about 90° C.), and enzymatic treatments (e.g., using hydrolyase, glycosidase, or glucocidase); and as such, components of the seed isolate can undergo esterification, transesterification, isomeric conversion, acetal formation, acetal decomposition, and the like. Additionally, various isolated lipid components of the seed can be subjected to hydrogenation in order to alter the degree of saturation of those components, and hence alter the physical form or behavior of those components.

In one aspect, seed can be cold pressed in order to squeeze lipids from the seed, and those lipid components are collected and isolated; or alternatively the seed can be subjected to solvent extraction using a solvent (e.g., a polar solvent or a non-polar organic solvent), and the resulting extract is collected and the extracted components are isolated. Then, the various seed components are subjected to enzymatic treatment to form an enzymatically-treated seed material. The enzymatically-treated material then is subjected to solvent extraction to form a seed isolate.

In one embodiment, the separating or isolating process comprises freezing a harvested seed or a portion thereof to form a frozen seed material, processing the frozen seed into a particulate form, subjecting the particulate seed material to an enzymatic treatment to chemically alter the particulate seed material, and extracting the particulate seed material with a solvent to produce a seed isolate. Exemplary enzymatic treatments include treatment with a glycosidase or a glucocidase.

The seeds and components of seed isolates are useful as components for tobacco compositions, particularly tobacco compositions incorporated into smoking articles or smokeless tobacco products. Addition of the seed components of the invention to a tobacco composition can enhance a tobacco composition in a variety of ways, depending on the nature of the seed isolate and the type of tobacco composition. Exemplary seed components can serve to provide flavor and/or aroma to a tobacco product (e.g., composition that alters the sensory characteristics of tobacco compositions or smoke derived therefrom).

The form of the seed isolate can vary. Typically, the seed isolate is in a solid, liquid, or semi-solid or gel form. The seed isolate can be used in concrete, absolute, or neat form. The seed isolate can have a dry particulate form, a waxy form, or a thick paste form. Liquid forms of the seed isolate include isolates contained within aqueous or organic solvent carriers.

The seed, processed seed and seed isolates can be employed in a variety of forms. The harvested seed or seed isolate can be employed as a component of processed tobaccos. In one regard, the seed, or components thereof, can be employed within a top dressing formulation, or within a casing formulation for application to tobacco strip (e.g., using the types of manners and methods set forth in U.S. Pat. No. 4,819,668 to Shelar, which is incorporated herein by reference). Alternatively, the seed, or components thereof, can be employed as an ingredient of a reconstituted tobacco material (e.g., using the types of tobacco reconstitution processes generally set forth in U.S. Pat. No. 5,143,097 to Sohn; U.S. Pat. No. 5,159,942 to Brinkley et al.; U.S. Pat. No. 5,598,868 to Jakob; U.S. Pat. No. 5,715,844 to Young; U.S. Pat. No. 5,724,998 to Gellatly; and U.S. Pat. No. 6,216,706 to Kumar, which are incorporated herein by reference). The seed, or components thereof, also can be incorporated into a cigarette filter (e.g., in the filter plug, plug wrap, or tipping paper) or incorporated into cigarette wrapping paper, preferably on the inside surface, during the cigarette manufacturing process. The seed isolate having a waxy or smooth texture can be used as a coating for the surface of a formed smokeless tobacco product. The seed isolate having sticky properties can be used as an adhesive (or component of an adhesive) or binding agent within tobacco products. The seed isolate having a oily or liquid character can be used as a solvent (e.g., to be used to replace, or act comparable to, a triglyceride type of solvent; or to replace a glycol type of solvent as a humectant or as a carrier for casing components).

The seed, processed seed and seed isolates can be incorporated into smoking articles. The seed, processed seed and seed isolates can be admixed with other components that are employed in the manufacture of tobacco products. Exemplary types of further ingredients that can be admixed with the seed material include flavorants, fillers, binders, pH adjusters, buffering agents, colorants, disintegration aids, antioxidants, humectants and preservatives. Representative tobacco blends, non-tobacco components, and representative cigarettes manufactured therefrom, are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,220,930 to Gentry; and U.S. Pat. No. 5,360,023 to Blakley et al.; US Pat. Appl. Pub. No. 2002/0000235 to Shafer et al.; and PCT WO 02/37990. Those tobacco materials also can be employed for the manufacture of those types of cigarettes that are described in U.S. Pat. No. 4,793,365 to Sensabaugh; U.S. Pat. No. 4,917,128 to Clearman et al.; U.S. Pat. No. 4,947,974 to Brooks et al.; U.S. Pat. No. 4,961,438 to Korte; U.S. Pat. No. 4,920,990 to Lawrence et al.; U.S. Pat. No. 5,033,483 to Clearman et al.; U.S. Pat. No. 5,074,321 to Gentry et al.; U.S. Pat. No. 5,105,835 to Drewett et al.; U.S. Pat. No. 5,178,167 to Riggs et al.; U.S. Pat. No. 5,183,062 to Clearman et al.; U.S. Pat. No. 5,211,684 to Shannon et al.; U.S. Pat. No. 5,247,949 to Deevi et al.; U.S. Pat. No. 5,551,451 to Riggs et al.; U.S. Pat. No. 5,285,798 to Banerjee et al.; U.S. Pat. No. 5,593,792 to Farrier et al.; U.S. Pat. No. 5,595,577 to Bensalem et al.; U.S. Pat. No. 5,816,263 to Counts et al.; U.S. Pat. No. 5,819,751 to Barnes et al.; U.S. Pat. No. 6,095,153 to Beven et al.; U.S. Pat. No. 6,311,694 to Nichols et al.; and U.S. Pat. No. 6,367,481 to Nichols et al.; US Pat. Appl. Pub. No. 2008/0092912 to Robinson et al.; and PCT WO 97/48294 and PCT WO 98/16125. See, also, those types of commercially marketed cigarettes described *Chemical and Biological Studies on New Cigarette Prototypes that Heat Instead of Burn Tobacco*, R. J. Reynolds Tobacco Company Monograph (1988) and *Inhalation Toxicology*, 12:5, p. 1-58 (2000).

The *Nicotiana* seed, processed seed, and seed isolates can be incorporated into smokeless tobacco products, such as loose moist snuff, loose dry snuff, chewing tobacco, pelletized tobacco pieces (e.g., having the shapes of pills, tablets, spheres, coins, beads, obloids or beans), extruded or formed tobacco strips, pieces, rods, cylinders or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips (e.g., US Pat. App. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtoniam fluid or a thixotropic fluid incorporating tobacco of some form). Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. App. Pub. Nos. 2005/0244521 to Strickland et al. and 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See also, the types of smokeless tobacco formulations, ingredients, and processing methodologies set forth in U.S. Pat. No. 6,953,040 to Atchley et al. and U.S. Pat. No. 7,032,601 to Atchley et al.; US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

The residue of seed material remaining after subjecting seed material to a separation process (e.g., cold pressing or solvent extraction) and removing some portion of the seed can also be incorporated into a tobacco product, including any of the tobacco products mentioned herein with regard to seed or seed isolates. For example, a seed residue remaining after cold pressing the seed and removing lipid components could be used as a tobacco composition component (e.g., as part of a reconstituted tobacco material), and incorporated into a smoking article or a smokeless tobacco composition. The insoluble pulp residue remaining after solvent extraction of a solvent-soluble portion of a seed material could likewise be used as a component of a tobacco composition.

Certain seed isolates, such as triglyceride-containing seed isolates, can be used as components of capsules used in smoking articles or smokeless tobacco compositions. In particular, triglyceride-containing seed isolates could be combined with a flavorant and used as a diluting agent or carrier within the internal payload of certain breakable capsules. Typically, a capsule of the type used in the invention has an outer wall and an internal liquid, solid, or gel payload. The payload is released upon rupture of the capsule wall. Exemplary capsule-containing tobacco products that could incorporate such seed isolates are set forth in US Pat. Appl. Pub. Nos. 2004/0261807 to Dube et al.; 2005/0066982 to Clark et al.; 2007/0186941 to Holton et al.; 2008/0302373 to Stokes et al.; and 2009/0050163 to Hartmann et al., each of which is incorporated herein by reference.

The amount of seed or seed isolate incorporated within a tobacco composition, or otherwise incorporated within a tobacco product, can depend on the desired function of that seed component, the chemical makeup of that component, and the overall type of tobacco composition. The amount incorporated within a tobacco composition can vary, but will typically not exceed about 5 weight percent, based on the total dry weight of the tobacco composition to which the seed or seed isolate is incorporated. When the seed is employed within a smoking article, the amount of seed typically is at least about 5 ppm, generally at least about 10 ppm, and often at least about 100 ppm, based on the total dry weight of the tobacco material within the smoking article; but typically is less than about 5 percent, generally less than about 2 percent, and often less than about 1 percent, based on the total dry weight of the tobacco material within the smoking article. When the seed is employed within a smokeless tobacco product, the amount of seed typically is at least about 5 ppm, generally at least about 10 ppm, and often at least about 100 ppm, based on the total dry weight of the tobacco material within the smokeless tobacco product; but typically is less than about 5 percent, generally less than about 2 percent, and often less than about 1 percent, based on the total dry weight of the tobacco material within the smokeless tobacco product.

Aspects of the present invention are more fully illustrated by the following example, which is set forth to illustrate certain aspects of the present invention and is not to be construed as limiting thereof.

Mature seeds from a Virginia tobacco plant are collected from the plant. About 1 gram of tobacco seeds and about 2.5 grams of diatomaceous earth (available from Acros Organics) are dry ground using a mortar and pestle. The ground mixture is transferred to a 22-ml, stainless-steel extraction cell. The remaining void space within the cell is filled with 3-mm diameter glass beads. The extraction cell is closed and placed on the cell rack of an accelerated solvent extraction instrument (i.e., an ASE 350 available from Dionex Corporation). The extraction conditions that are used are based on Extraction of Oils from Oilseeds by Accelerated Solvent Extraction (ASE®), Application Note 325, Dionex Corporation. After extraction is complete, the extraction cell is placed in a TurboVapII (available from Zymark Corporation) and operated using dry nitrogen for 90 minutes to evaporate virtually all of the solvent.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method for preparing a seed isolate derived from a seed of the *Nicotiana* species for addition to a tobacco composition, comprising:
    isolating components of a harvested seed of the *Nicotiana* species by subjecting the harvested seed or a portion thereof to cold pressing, solvent extraction, chromatography, distillation, filtration, recrystallization, solvent-solvent partitioning, or a combination thereof to form a seed isolate,
    chemically transforming the harvested seed prior to said isolating step or chemically transforming the seed isolate after said isolating step, wherein the chemically transforming step is a treatment selected from the group consisting of hydrogenation, acid/base reaction, hydrolysis, thermal treatment, enzymatic treatment, or a combination thereof, and
    adding a chemically transformed seed isolate to a tobacco composition adapted for use in a smoking article or a smokeless tobacco composition.

2. The method of claim 1, wherein the isolating step comprises solvent extraction of a harvested seed or a portion thereof using a solvent.

3. The method of claim 1, wherein said chemically transforming step comprises subjecting the harvested seed or a portion thereof to enzymatic treatment to form an enzymatically-treated seed material, and said isolating step comprises subjecting the enzymatically-treated seed material to solvent extraction to form a chemically transformed seed isolate.

4. The method of claim 1, wherein said chemically transforming step comprises freezing a harvested seed or a portion thereof to form a frozen seed material, processing the frozen seed into a particulate form, and subjecting the particulate seed material to an enzymatic treatment to chemically alter the particulate seed material, and wherein said isolating step comprises extracting the particulate seed material with a solvent to produce a chemically transformed seed isolate.

5. The method of claim 1, wherein said chemically transforming step comprises enzymatic treatment of the harvested seed or a portion thereof with a hydrolyase, a glycosidase, or a glucocidase.

6. The method of claim 1, wherein said isolating step comprises cold pressing the harvested seed or a portion thereof in order to express lipids from the harvested seed to form a lipid-containing seed isolate.

7. The method of claim 6, wherein said chemically transforming step comprises subjecting the lipid-containing seed isolate to hydrogenation in order to alter the degree of saturation of the lipids within the lipid-containing seed isolate.

8. The method of claim 1, further comprising, prior to said isolating step, subjecting the harvested seed or a portion thereof to a treatment selected from the group consisting of refrigerating, freezing, freeze drying, irradiation, yellowing, drying, curing, and cooking.

9. A method for preparing a seed isolate derived from a seed of the *Nicotiana* species for addition to a tobacco composition, comprising:
  chemically transforming a harvested seed of the *Nicotiana* species, wherein the chemically transforming step comprises freezing a harvested seed or a portion thereof to form a frozen seed material, processing the frozen seed into a particulate form, and subjecting the particulate seed material to an enzymatic treatment to chemically alter the particulate seed material, and
  isolating components of the harvested seed of the *Nicotiana* species, wherein said isolating step comprises extracting the particulate seed material with a solvent to produce a chemically transformed seed isolate.

10. A method for preparing a seed isolate derived from a seed of the *Nicotiana* species for addition to a tobacco composition, comprising:
  isolating components of a harvested seed of the *Nicotiana* species by subjecting the harvested seed or a portion thereof to cold pressing, solvent extraction, chromatography, distillation, filtration, recrystallization, solvent-solvent partitioning, or a combination thereof to form a seed isolate, and
  chemically transforming the harvested seed prior to said isolating step or chemically transforming the seed isolate after said isolating step, wherein the chemically transforming step comprises enzymatic treatment of the harvested seed or a portion thereof with a hydrolyase, a glycosidase, or a glucocidase.

11. A method for preparing a seed isolate derived from a seed of the *Nicotiana* species for addition to a tobacco composition, comprising:
  isolating components of a harvested seed of the *Nicotiana* species by subjecting the harvested seed or a portion thereof to cold pressing, solvent extraction, chromatography, distillation, filtration, recrystallization, solvent-solvent partitioning, or a combination thereof to form a seed isolate, wherein said isolating step comprises cold pressing the harvested seed or a portion thereof in order to express lipids from the harvested seed to form a lipid-containing seed isolate, and
  chemically transforming the seed isolate after said isolating step, wherein said chemically transforming step comprises subjecting the lipid-containing seed isolate to hydrogenation in order to alter the degree of saturation of the lipids within the lipid-containing seed isolate.

* * * * *